US006559446B1

(12) United States Patent
Choo et al.

(10) Patent No.: US 6,559,446 B1
(45) Date of Patent: May 6, 2003

(54) SYSTEM AND METHOD FOR MEASURING DIMENSIONS OF A FEATURE HAVING A RE-ENTRANT PROFILE

(75) Inventors: Bryan K. Choo, Mountain View, CA (US); Bhanwar Singh, Morgan Hill, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 280 days.

(21) Appl. No.: 09/670,775

(22) Filed: Sep. 27, 2000

Related U.S. Application Data
(60) Provisional application No. 60/213,032, filed on Jun. 21, 2000.

(51) Int. Cl.[7] .............................................. G01N 23/225
(52) U.S. Cl. ...................................... 250/310; 250/307
(58) Field of Search ................................ 250/306–307, 250/310–311

(56) References Cited

U.S. PATENT DOCUMENTS 5,029,250 A * 7/1991 Komatsu et al. ............ 250/310

OTHER PUBLICATIONS

"About CD–SEM Technology", *Applied Materials, Products and Services, PDC*, taken from the Internet at: http://www.appliedmaterials.com/products/about_cdsem.html, one page.
"CD–SEM (Critical Dimension Scanning Electron Microscope)", *Applied Materials, Products and Services, PDC*, taken from the Internet at: http://www.appliedmaterials.com/products/cdsem.html, one page.

* cited by examiner

*Primary Examiner*—John R. Lee
*Assistant Examiner*—Christopher M. Kalivoda
(74) *Attorney, Agent, or Firm*—Eschweiler & Associates, LLC

(57) ABSTRACT

A system and method are disclosed for measuring and/or imaging a feature having a re-entrant cross-sectional profile. Beams are emitted onto the feature and substrate at different angles during corresponding measurement intervals. An feature data set of the feature is characterized for each measurement interval. The data associated with each measurement interval are aggregated to provide a cross-sectional representation of the having dimensions proportional to the feature. As a result, a more accurate feature profile may be determined, including a cross-sectional dimension of the re-entrant feature at the juncture between the feature and substrate.

22 Claims, 9 Drawing Sheets

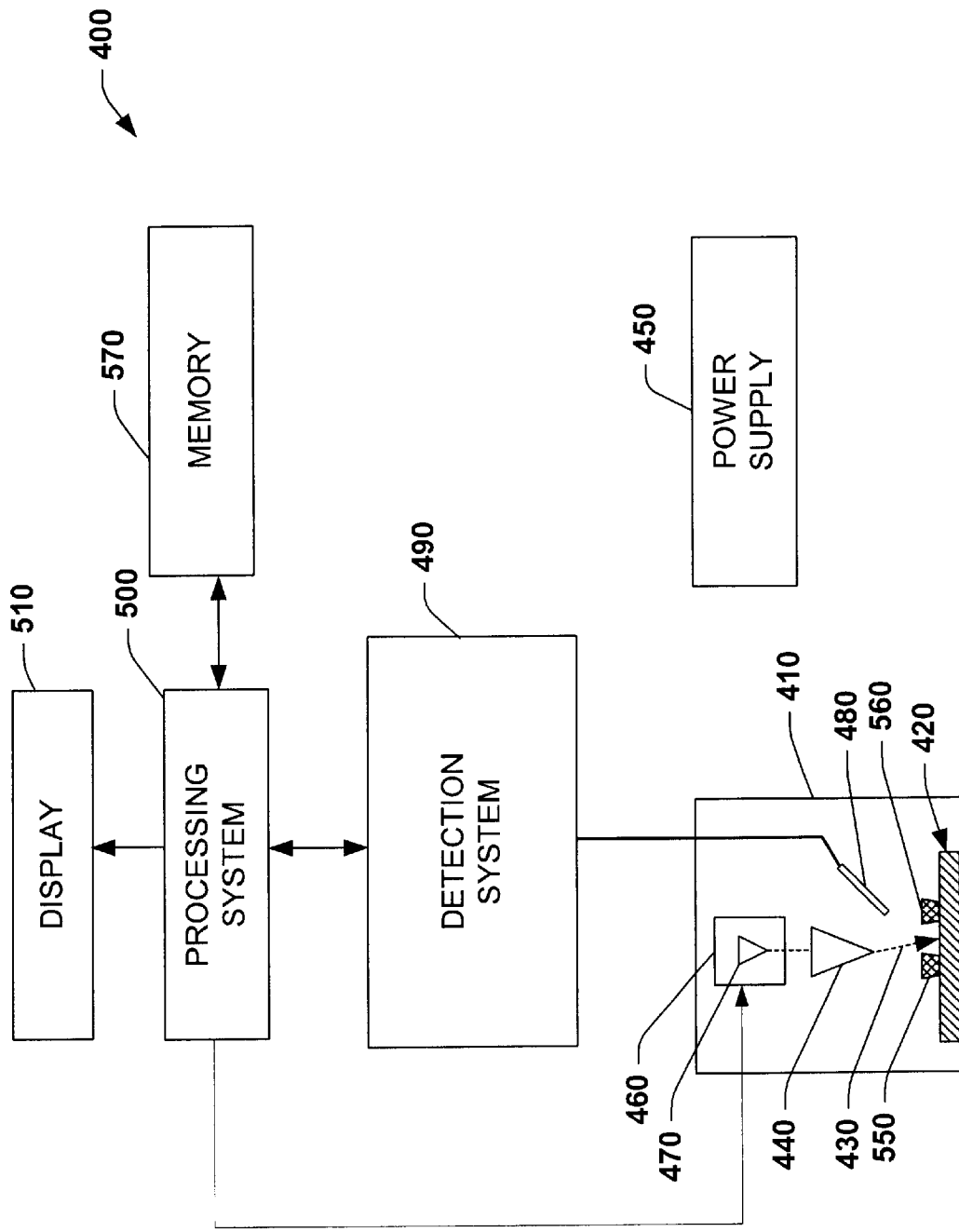

SYSTEM AND METHOD FOR MEASURING DIMENSIONS OF A FEATURE HAVING A RE-ENTRANT PROFILE

RELATED APPLICATION

This application claims priority to the provisional application Serial No. 60/213,032 filed Jun. 21, 2000, which is entitled "System and Method for Measuring Dimensions of a Feature Having a Re-Entrant Profile".

FIELD OF THE INVENTION

The present invention generally relates to semiconductor processing and, more particularly, to a system and method for measuring and/or imaging features, such as lines and spaces, including those having a re-entrant profile.

BACKGROUND OF THE INVENTION

In the semiconductor industry, there is a continuing trend toward higher device densities. To achieve these high densities there has been and continues to be efforts toward scaling down the device dimensions on semiconductor wafers (e.g., at submicron levels). In order to accomplish such high device packing density, smaller and smaller features sizes are required. This may include the width and spacing of interconnecting lines, spacing and diameter of contact holes, and the surface geometry such as corners and edges of various features.

The requirement of small features with close spacing between adjacent features requires high resolution photolithographic processes. In general, lithography refers to processes for pattern transfer between various media. It is a technique used for integrated circuit fabrication in which a silicon slice, the wafer, is coated uniformly with a radiation-sensitive film, the resist, and an exposing source (such as optical light, x-rays, etc.) illuminates selected areas of the surface through an intervening master template, the mask, for a particular pattern. The lithographic coating is generally a radiation-sensitive coating suitable for receiving a projected image of the subject pattern. Once the image is projected, it is indelibly formed in the coating. The projected image may be either a negative or a positive image of the subject pattern. Exposure of the coating through a photomask causes the image area to become either more or less soluble (depending on the coating) in a particular solvent developer. The more soluble areas are removed in the developing process to leave the pattern image in the coating as less soluble polymer.

Due to the extremely fine patterns which are exposed on the photoresist, Scanning Electron Microscopes (SEMs) often are employed to analyze and measure critical dimensions resulting from the lithographic process. Critical dimensions include the size of minimum features across the wafer such as linewidth, spacing, and contact dimensions.

In certain fabrication processes, resist and/or etched features have cross-sectional profiles that are re-entrant. By "re-entrant profile," it is meant that the sidewalls of the feature taper inwardly at the bottom of the feature. For an elongated feature, such as a line or space, a re-entrant profile may result in an elongated trench (e.g., having a triangular cross section) positioned along the juncture of the feature and the substrate surface parallel to the substrate surface. While the re-entrant profile may be desirable in certain circumstances, the re-entrant features may cause a shadowing effect during subsequent deposition. As a result of the shadowing effect by the upper portion of the feature, an elongated void may be formed during the deposition at the bottom surface of the re-entrant feature in contact with the substrate. The void, if undetected, may have serious consequences for subsequent processing steps and may result in defects that compromise the operation of the resulting semiconductor device. Conventional SEM systems for measuring critical dimensions of wafers often fail to detect re-entrant profiles of lines and/or spaces, as they tend to employ top-down electron beams or a beam that is electronically tilted at a predetermined angle relative to the substrate.

It is desirable to have a system and/or method which facilitates measuring and/or imaging a feature, such as a line and/or space, having a re-entrant profile.

SUMMARY OF THE INVENTION

The present invention relates to a system and method for measuring and/or imaging a feature having a re-entrant cross-sectional profile. Beams are emitted onto the feature and substrate at at least two different angles during corresponding measurement intervals, such as by employing a scan-tilt CD-SEM. A feature data set for the feature is characterized for each measurement interval. The data sets associated with each measurement interval are aggregated to provide a cross-sectional representation of the feature. Because beams are emitted at different relative angles during the measurement intervals, each corresponding data set represents feature characteristics according to portions of the feature that the beam strikes. As a result, a more accurate feature profile may be determined, including a cross-sectional dimension of the feature at the juncture between the feature and substrate.

One aspect of the present invention relates to a method for measuring a cross-sectional profile of a feature in a substrate. The method includes the steps of performing first and second scans of the feature at different angles relative to the substrate to provide respective first and second feature data sets, such that an aggregate of the first and second feature data sets indicates the feature profile.

Another aspect of the present invention relates to a system for determining a cross-sectional profile of a feature in a substrate. An emitter directs a beam onto the substrate at a first angle during a first measurement interval and at a second angle, which is different from the first angle, during a second measurement interval. A detector detects interactions between the beam and the feature and/or substrate and provides a detector signal indicative thereof. A controller determines a first feature data set based on the detector signal associated with the first measurement interval and a second feature data set based on the detector signal associated with the beam during the second measurement interval. The controller then determines a cross-sectional characteristic of the feature based on the first and second feature data sets.

Yet another aspect of the present invention relates to a CD-SEM system primarily for measuring a cross-sectional dimension of a feature having a re-entrant profile relative to a substrate. A lens is provided for directing electrons to the surface of the substrate at a first angle during a first scanning interval and at a second angle during a second scanning interval, the second angle being different from the first angle relative to the substrate. A detector provides a signal based upon electrons received from the surface of the wafer. A processing system determines a first feature data set based on detected electrons associated with the first scanning interval and a second feature data set based on detected electrons associated with the second scanning interval. The processing system determines a cross-sectional characteristic of the feature based on an aggregation of the first and second feature data sets.

To the accomplishment of the foregoing and related ends, the invention, then, comprises the features hereinafter fully described. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1b is an example of an expected cross-sectional representation of the scanned feature of FIG. 1a;

FIG. 3b is a graphical representation of a cross-section constructed from the scanning of FIG. 3a;

FIG. 4 is a system block diagram of a feature dimension measurement system in accordance with the present invention.

DETAILED DESCRIPTION OF THE INVENTION

Figure 1A:
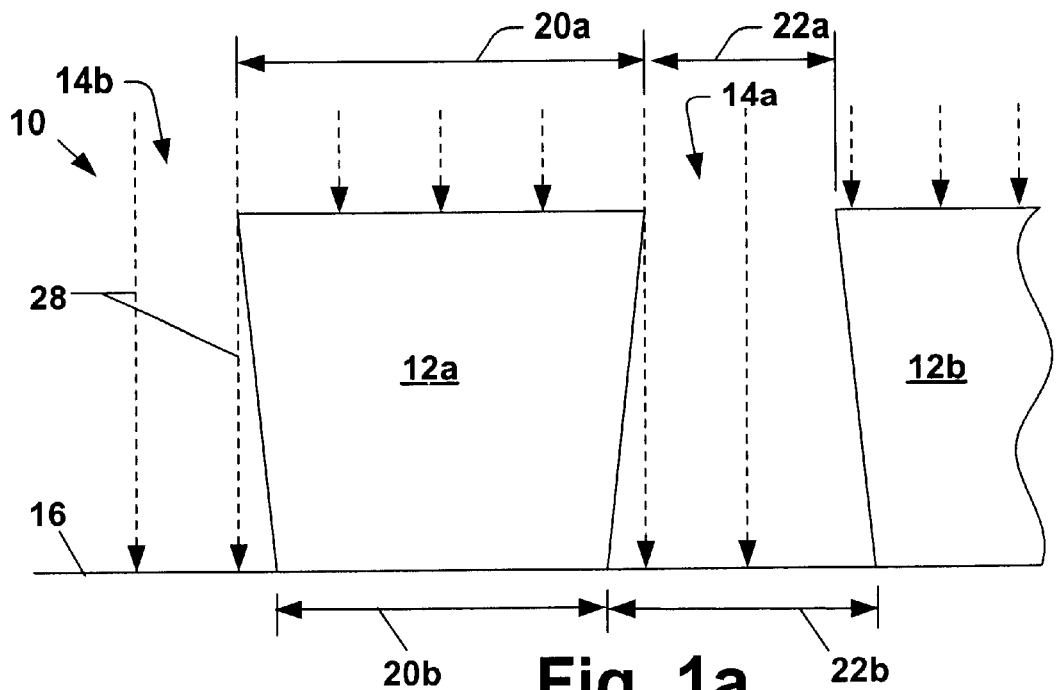
FIG. 1a is a cross-sectional view of a wafer feature illustrating a prior art approach of scanning critical dimension measurements.

The present invention will now be described with reference to the drawings, wherein like reference numerals are used to refer to like elements throughout.

The present invention provides a system and methodology to detect cross-sectional dimensions of a feature relative to a substrate. The system is implemented, for example, as part of a critical dimension scanning electron microscope (CD-SEM). Although the present invention is described in reference to a CD-SEM system, it is to be appreciated that the system and methodology described below may be applied to substantially any measurement system which employs a beam to measure and/or image topographical features.

Prior art FIG. 1a illustrates a cross-section of a printed wafer 10 having a plurality of features, including lines 12a and 12b and intermediate open regions or spaces 14a and 14b. The features have been patterned on or in an associated substrate to have re-entrant profiles, in which sidewalls of the lines 12a and 12b taper inwardly at the bottom of the respective features. As such, corresponding critical dimensions of the features 12–14 near the substrate 16 differ from their corresponding critical dimensions distal the substrate. In particular, an upper linewidth dimension 20a of line 12a is greater than its lower linewidth dimension 20b (upper and lower being relative terms to describe feature dimensions illustrated according to FIG. 1a). Similarly, the adjacent space 14a has a cross-sectional shape, in which its upper critical dimension 22a is less than its lower critical dimension 22b.

Prior art FIG. 1a further illustrates a conventional approach for measuring critical dimensions of the wafer 10. A beam line 28 (e.g., an electron beam emitted by a SEM or like system) is emitted substantially perpendicular relative to the substrate 16 and traverses a path across the wafer. For purposes of clarity, the beam line 28 is illustrated as a series of beam lines along a scan line extending across a surface of a feature. Because the beam line 28 is provided in a top-down manner, the lower dimensions 20b and 22b are not measured and/or imaged accurately, as they are shadowed by the upper portions of adjacent lines.

Figure 1B:
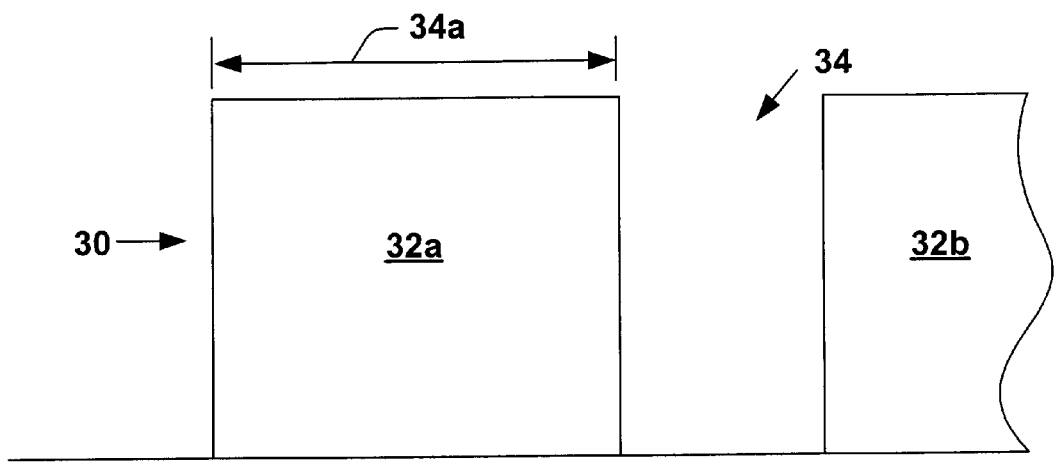

Prior art FIG. 1b illustrates an example of a cross-sectional representation 30 constructed based on the information collected from the scanning methodology illustrated in prior art FIG. 1a. The representation 30 includes portions 32a and 32b corresponding to the respective lines 12a and 12b (FIG. 1a) with an intermediate space 34 located therebetween corresponding to space 14a. The portion 32a is depicted as a rectangle having a constant width corresponding to the upper dimension 34a (FIG. 1a). While the conventional methodology is able to collect image data indicative of upper feature dimensions, it is unable to acquire data concerning lower feature dimensions that are shadowed by the upper feature portions. Because of the shadowing effect of the re-entrant profile features, there are no representations in the cross-section 30 which correspond to the lower dimensions of the wafer features. As a result of not being able to accurately detect and/or measure a re-entrant profile, subsequent processing (e.g., deposition, etching, etc.) may develop voids or channels along the line features, which may adversely affect operation of the resulting semiconductor structure.

Figure 2A:
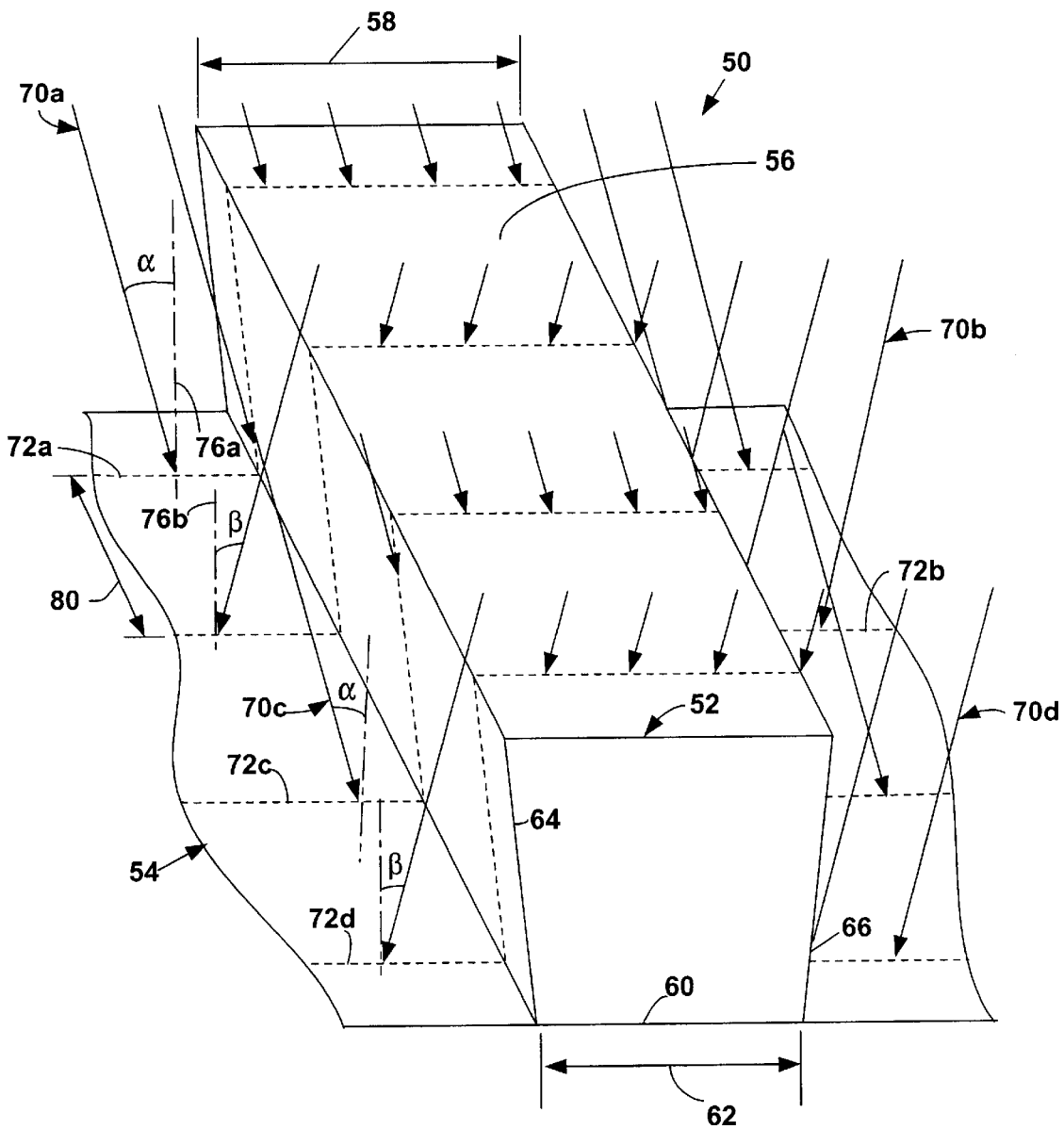
FIG. 2a is an isometric view of a wafer feature being scanned in accordance with the present invention.

FIG. 2a illustrates an example of an isometric view of part of a printed wafer 50 which includes an elongated feature in the form of a line 52 having a re-entrant profile relative to a substrate 54. The line 52 includes an upper portion 56 having an upper linewidth dimension 58 spaced apart from a lower portion 60 at the juncture between the line and the substrate. The lower portion 60 has a linewidth dimension 62 that is less than the upper linewidth dimension 58. Sidewall portions 64 and 66 extend between the upper and lower portions 56 and 60, respectively. While, for purposes of simplicity of illustration, the line 52 is illustrated as being substantially linear, it is to be appreciated that other line shapes and other-feature types may be employed in accordance with the present invention.

FIG. 2a further diagrammatically illustrates a methodology for imaging and/or measuring critical dimensions of features on the wafer 50 in accordance with the present invention. A plurality of beam lines (e.g., electron beams) are directed at different scanning angles relative to the substrate 54 to enable measuring and/or imaging of each of the sidewall portions 64 and 66. In the example of FIG. 2a, alternating beam lines 70a, 70b, 70c, and 70d (hereinafter collectively referred to as beam lines 70) scan the feature and the substrate along corresponding spaced apart paths 72a, 72b, 72c, 72d for measuring and/or imaging the topography of the feature 52 and wafer 50 surface. While, for purposes of clarity, each beam line 70a, 70b, 70c, 70d is illustrated as series of beam lines along a respective scan line path 72a, 72b, 72c, 72d. it is to be understood and appreciated that the beam lines represent movement of a beam line (e.g., rastering of an electron beam) traversing the associated scan line path. In addition, while the scan line paths 72 are illustrated as being linear, other shapes of paths also may be employed in accordance with the present invention.

By way of example, the beam line 70a along the scan line 72a is directed onto the wafer 50 surface at an angle $\alpha$ relative to an imaginary line 76a drawn perpendicular to the substrate 54. The beam line 70a sweeps across the feature 52 along the path indicated at 72a for collecting measurement data corresponding to feature structures. The beam line 70a interacts with the wafer 50, including the feature 52 and substrate 54. The surface interactions are monitored by an associated detection system (see, e.g., FIG. 4) which determines an image indicative of the surface topography based on the interactions.

Another beam line 70b similarly is directed onto the wafer surface at an angle $\beta$ relative to a line 76b perpendicular to the substrate over a next measurement interval. For example, the angle $\beta$ is substantially opposite the angle $\alpha$ relative to the substrate surface (e.g., $\beta \approx -\alpha$). The beam line 70b scans across the wafer 50 surface along another path 72b. The scan line path 72b is spaced apart from the path 72a by a preselected interval 80. The interval 80 between adjacent scan lines 72a and 72b has been exaggerated for purposes of simplicity of illustration, as the distance between adjacent scan lines typically is kept to a minimum defined by the resolution of the scanning tool.

It is to be appreciated to those skilled in the art that each beam line 70 may be in the form of constant or pulsed beam that traverses its associated path 72. It is further to be appreciated that the spacing between adjacent pairs of the beam lines 70 on each respective scan line path 72 is shown for purposes of ease of illustration, as any spacing interval may be utilized and is contemplated as falling within the scope of the present invention.

The beam lines 70c and 70d each scan and interact with the wafer surface in a manner similar to that previously described with respect to lines 70a and 70b. Briefly stated, the beam lines 70c and 70d scan the wafer surface along scan line paths 72c and 72d, respectively. The beam lines 70c and 70d are directed onto the wafer 50 surface at substantially the same relative angular orientation and frequency as the respective beam lines 70a and 70b. In this way, the beam lines 70 of alternating angular orientation relative to the wafer 50 surface are able to map the relative cross-sectional dimensions of the sidewall portions 64 and 66 to more accurately measure and, in turn, more accurately represent or quantify the elongated feature's cross-sectional re-entrant profile.

Figure 2B:
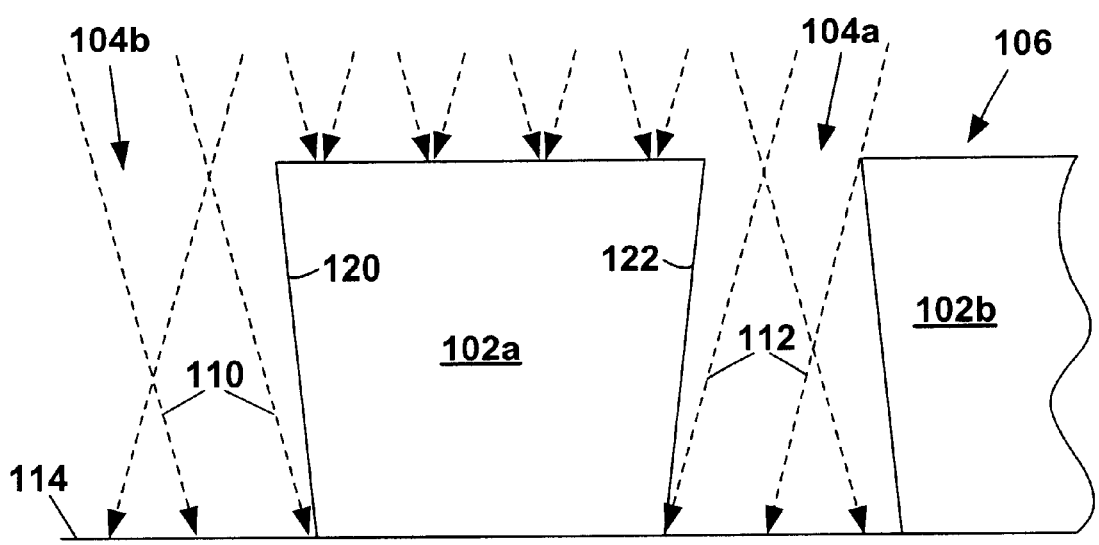
FIG. 2b is a cross-sectional view of a wafer feature illustrating scanning from two substantially opposite directions in accordance with the present invention.

An alternative methodology for measuring and/or imaging critical dimensions of features, including lines 102a and 102b and spaces 104a and 104b, associated with a wafer 106 surface is illustrated in FIG. 2b. In this approach, two beam lines 110 and 112 having different angular orientations relative to a substrate 114 are scanned along substantially the same scan line path. For example, the first beam line 110 is scanned across a path of the wafer surface at a predetermined angle relative to the substrate 114 over a first measurement interval. The second beam line 112 is scanned across the wafer 106 surface at a different predetermined angle relative to the substrate over a subsequent measurement interval. The angles, for example, are substantially opposite in magnitude relative to the wafer surface (e.g., about +5° and –5° relative to a line extending perpendicular to the wafer surface) so that each scan is able to obtain desired measurement data concerning the configuration and dimensions of a corresponding sidewall portion 120 and 122. An aggregate of the measurement data, in turn, provides an indication of the overall cross-sectional dimensions of the re-entrant feature 102a along the scan line path. By repeating this scanning methodology along a plurality of spaced apart scan lines along a feature, a substantially accurate graphical representation of the cross-sectional feature profile may be constructed.

FIGS. 3a–3g illustrate a methodology 200, in accordance with the present invention, for determining cross-sectional dimensions of a feature 210 having a re-entrant profile relative to a substrate 212. The feature 210 has respective upper and lower portions 214 and 216 spaced apart by sidewall portions 218 and 220. The distance between the sidewall portions 218 and 220 taper toward the lower feature portion 216. The upper and lower portions 214 and 216 have respective dimensions indicated at 222 and 224, in which the upper dimension is illustrated as being greater than the lower dimension.

Figure 3A:
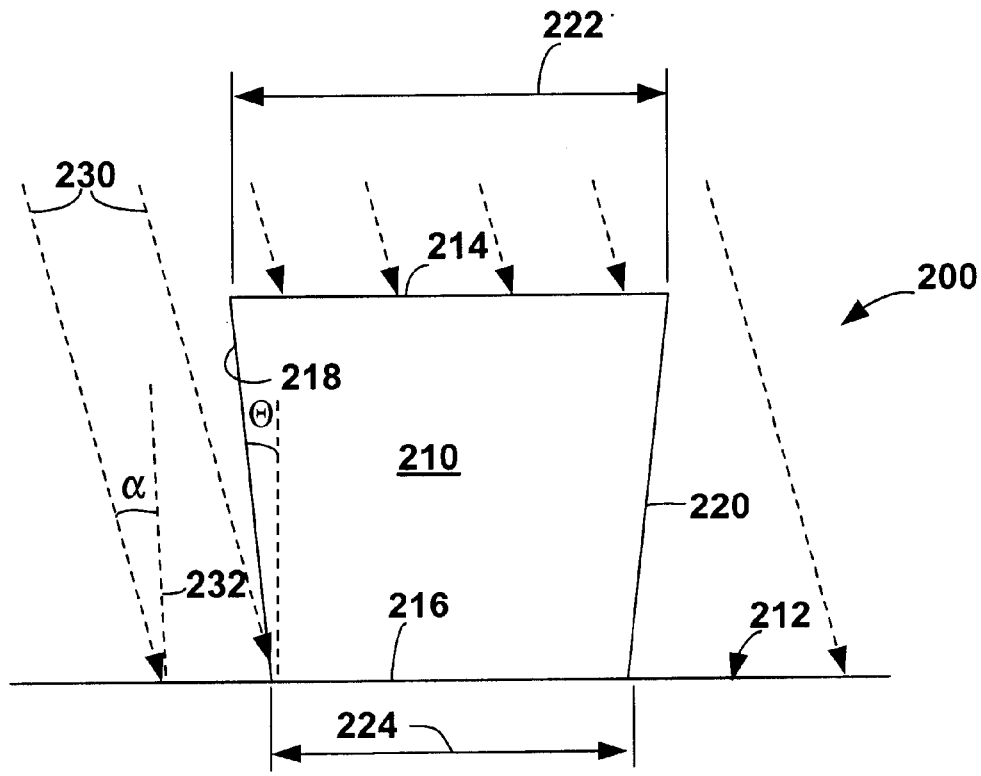
FIG. 3a is cross-sectional view of a wafer feature illustrating scanning a feature from a first direction in accordance with the present invention.

Referring to FIG. 3a, the feature 210 is scanned during a first measurement interval by a beam line 230 directed onto the wafer surface. Again, for purposes of clarity, the beam line 230 is illustrated as series of lines directed along a scan line path associated with the feature 210 and substrate 212. The beam line 230 is oriented at a predetermined angle $\alpha$ relative to a line 232 extending perpendicular to the substrate 212. It is to be appreciated that the angle $\alpha$ is greater than the relative angle $\theta$ between the sidewall 218 and the line 232. As a result, the beam line 230 is capable of striking the sidewall 218 and the juncture between the sidewall and the substrate so that an accurate cross-sectional profile of the left side of the feature 210 may be determined. Because the beam line 230 is provided at the angle $\alpha$ relative to the line 232 perpendicular to the substrate 212, however, it does not strike the opposite sidewall 220 of the feature.

Figure 3B:
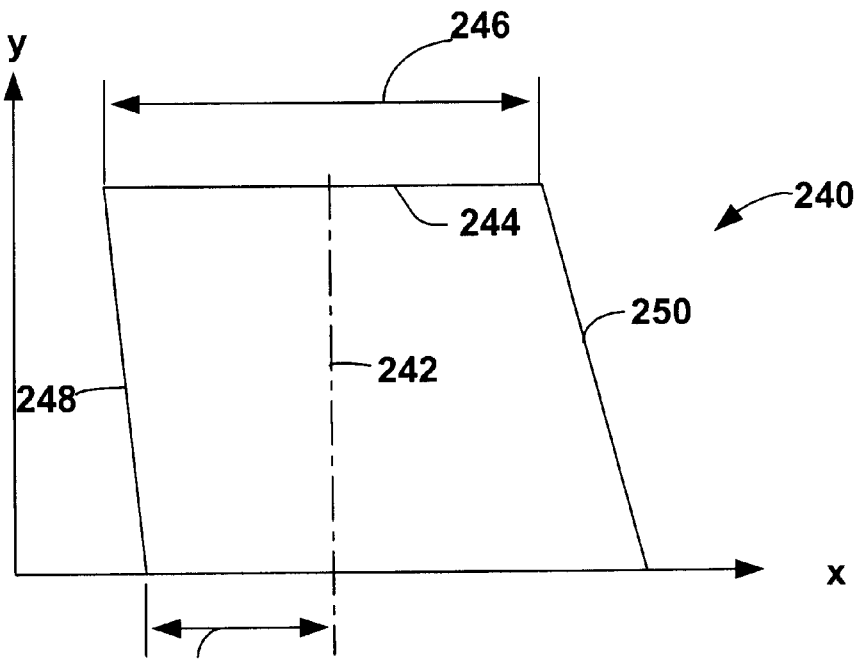

FIG. 3b illustrates a graphical representation a cross section 240 of the feature 210 according to the feature portions interacted with by the angled beam line 230 of FIG. 3a. A center line 242 has been drawn through the cross section 240 at about a midpoint of an upper portion 244 of the cross section 240. The upper portion 244 of the cross section 240 corresponds to the feature upper portion 214 (FIG. 3a) and has a dimension 246 which is proportional to the upper feature dimension 222 (FIG. 3a). The angular orientation of the beam line 230 also enables an accurate depiction of the sidewall 218 of the feature 210 (FIG. 3a), which is indicated at 248. The beam line 230 employed in FIG. 3a, however, results in an inaccurate representation 250 of the re-entrant profile associated with the sidewall portion 220 (FIG. 3a). Despite an inaccuracy depicted in a right-side portion 250 of the cross section 240, a left portion of the cross section (e.g., from the left of the center line 242) accurately represents of a corresponding part of the feature 210. In particular, the distance between the center line 242 and the lower edge of the sidewall 248, indicated at 254, is proportional to a corresponding part of the feature 210 of FIG. 3a (e.g., proportional to about ½ the lower feature dimension 224).

Figure 3C:
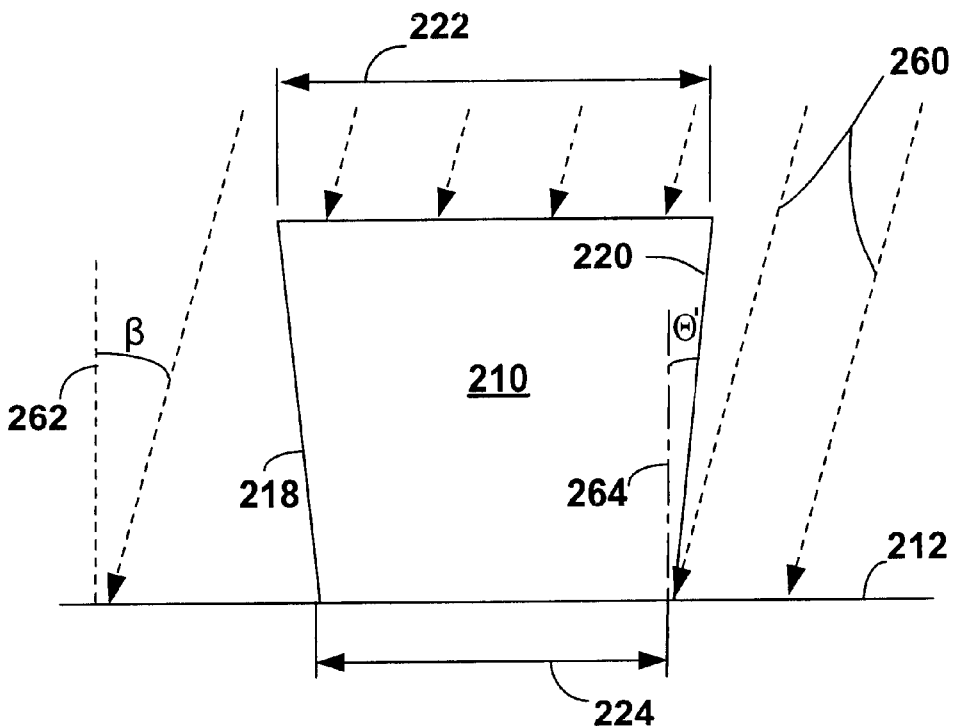
FIG. 3c is cross-sectional view of a wafer feature illustrating scanning a feature from a second direction in accordance with the present invention.

In order to accurately measure the other portion (e.g., right half) of the feature 210, the feature may be scanned during another scanning interval, such as illustrated in FIG. 3c. As mentioned above, the scanning during this interval may occur over substantially the same cross-sectional scan line path of the feature as scanned in FIG. 3a or over a path spaced a predetermined distance along the feature from where previously scanned. A beam line 260 is directed toward the feature 210 and the substrate 212 at a predetermined angle β relative to a line 262 extending perpendicular to the substrate. It is to be appreciated that the angle β is greater than the relative angle θ' between the sidewall 220 and another line 264 extending perpendicular to the substrate 212. As a result, the beam line 260 is capable of striking the sidewall 220 as well as the juncture between the sidewall and the substrate 212 so that an accurate cross-sectional profile of the right side of the feature 210 may be determined. Because the beam line 260 is provided at the angle β relative to the line 262, it is unable to strike the opposite sidewall 218.

Figure 3D:
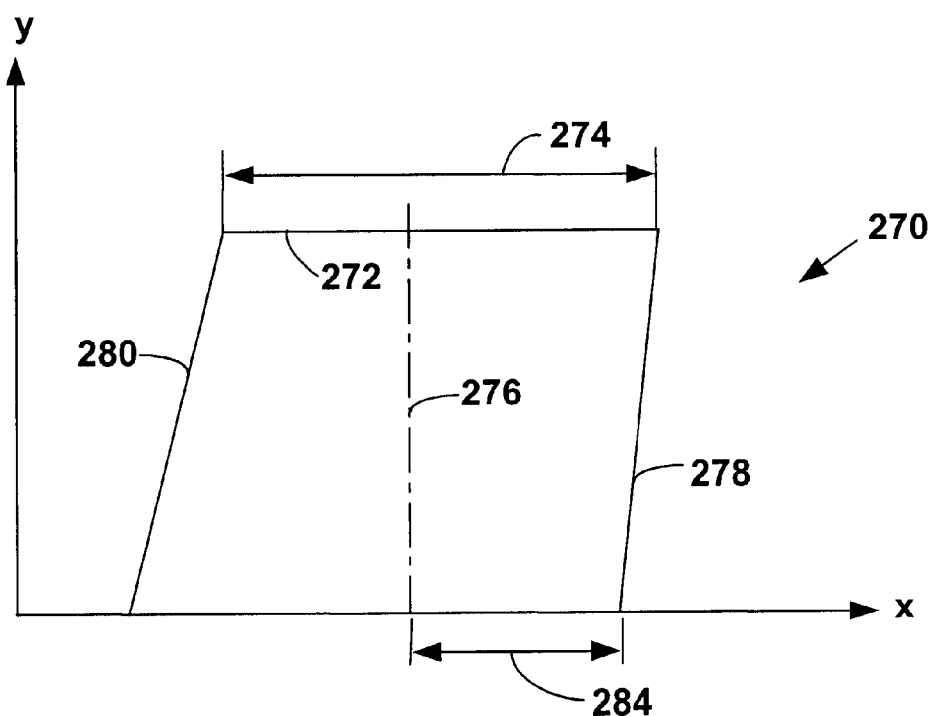
FIG. 3d is a graphical representation of a cross-section constructed from the scanning of FIG. 3c.

FIG. 3d is a graphical representation a cross section 270 of the feature 210 based interactions of the angled beam line 260 with the feature 210 and substrate 212 shown in FIG. 3c. Similar to FIG. 3b, an upper portion 272 of the cross section 270 corresponds to the feature upper portion 214 (FIG. 3c) and has a dimension 274 which is proportional to the upper feature dimension 222 (FIG. 3c). A center line 276 has been drawn perpendicular to an X-axis and through the cross section 270 at a midpoint of the upper portion 272. Because of the angular orientation of the beam line 260, a right side portion 278 of the cross section 270 accurately depicts the sidewall 220 of the feature 210 shown in FIG. 3c. In contrast, a left side 280 of the cross section provides an inaccurate representation of the left sidewall portion 218 of the feature 212 due to the angle at which the scan line 260 was provided (FIG. 3c), as it was unable to interact with the sidewall portion 218. While the cross section 270 inaccurately depicts the left sidewall 218 of the feature 210, a right half of the cross section (e.g., from the right of the center line 276) provides an accurate representation of a corresponding part of the feature 210. In particular, a distance, indicated at 284, between the center line 276 and the lower edge of the sidewall 248 is proportional to a corresponding part of the feature 210 of FIG. 3c (e.g., proportional to about ½ the lower feature dimension 224).

Figure 3E:
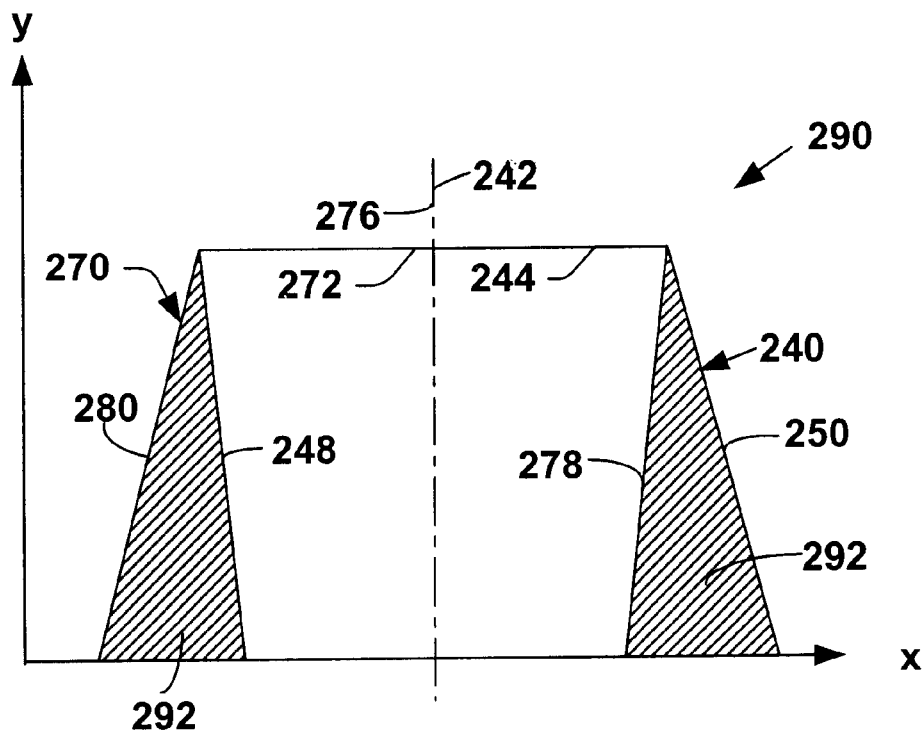
FIG. 3e is a graphical representation of an aggregation of the cross-sections of FIGS. 3b and 3d in accordance with the present invention.

FIG. 3e illustrates an aggregation (or overlay) 290 of the cross-sectional reconstructions of FIGS. 3b and 3d in which the center lines 242 and 276 of the respective cross sections 240 and 270 are aligned. The upper portions 244 and 272 of the respective cross sections 240 and 270 also are aligned, as they have substantially equal graphical proportions relative to the overlapping center lines 242 and 276.

Shaded regions 292 represent portions of each feature data set determined to be unreliable according to the scanning methodology employed. Because the side portions 248 and 278 also accurately depicts corresponding parts of the feature profile, the other side portions 250 and 280 (which are determined to be unreliable due the respective scanning angles) may be rejected or ignored from the aggregate reconstruction. Those skilled in the art will appreciate that the overlay/aggregation process may include graphical and/ or mathematical manipulation to aggregate the data and remove/ignore the portions corresponding to the shaded regions 292, all such techniques being within the scope of the present invention.

Figure 3F:
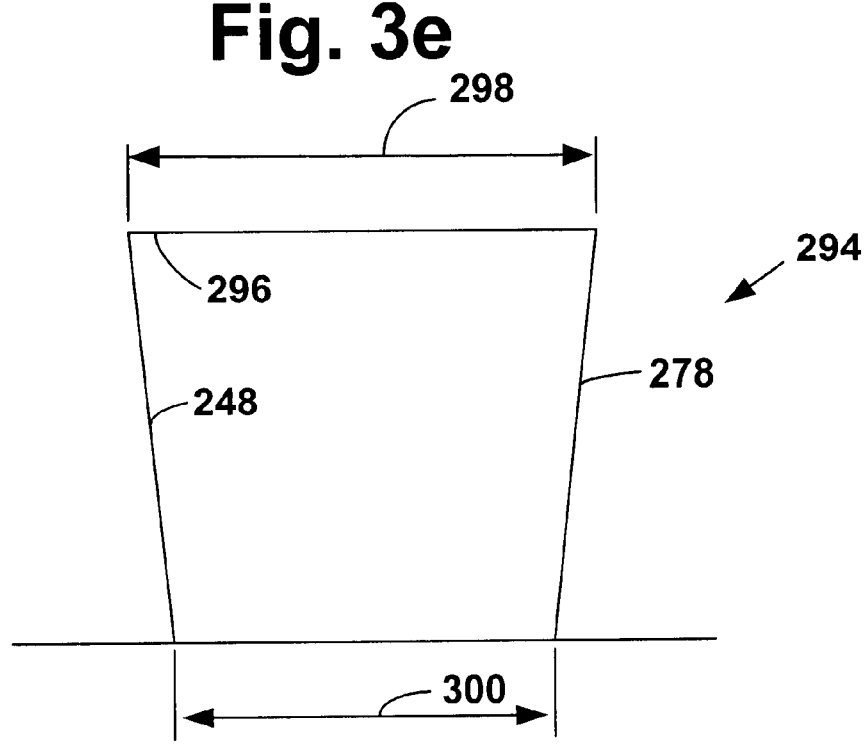
FIG. 3f is a graphical representation of a feature cross-section based on the aggregation of FIG. 3e in accordance with the present invention.

FIG. 3f illustrates a resulting aggregate reconstruction 294 after removing the shaded regions 292 from the aggregation 290 of FIG. 3e. The resulting reconstruction 294 accurately depicts the feature profile and includes the sidewall 248 from FIG. 3b, the sidewall 278 from FIG. 3d, and an upper portion 296, which is an aggregate of upper portions 244 (FIG. 3b) and 272 (FIG. 3d). The upper portion 296 has a linewidth dimension 298 that is proportional to the dimension of the corresponding feature part. Because the linewidth dimension 298 is derived from data obtained from two scanning intervals, mathematical interpolation or averaging may be employed to improve accuracy. The aggregation also produces an accurate representation of a critical dimension 300 of a lower portion of the feature, particularly at the juncture where the sidewalls meet the substrate. In this example, the resulting reconstruction illustrates a re-entrant profile for the feature, with the upper dimension 298 being greater than the lower dimension 300.

Figure 3G:
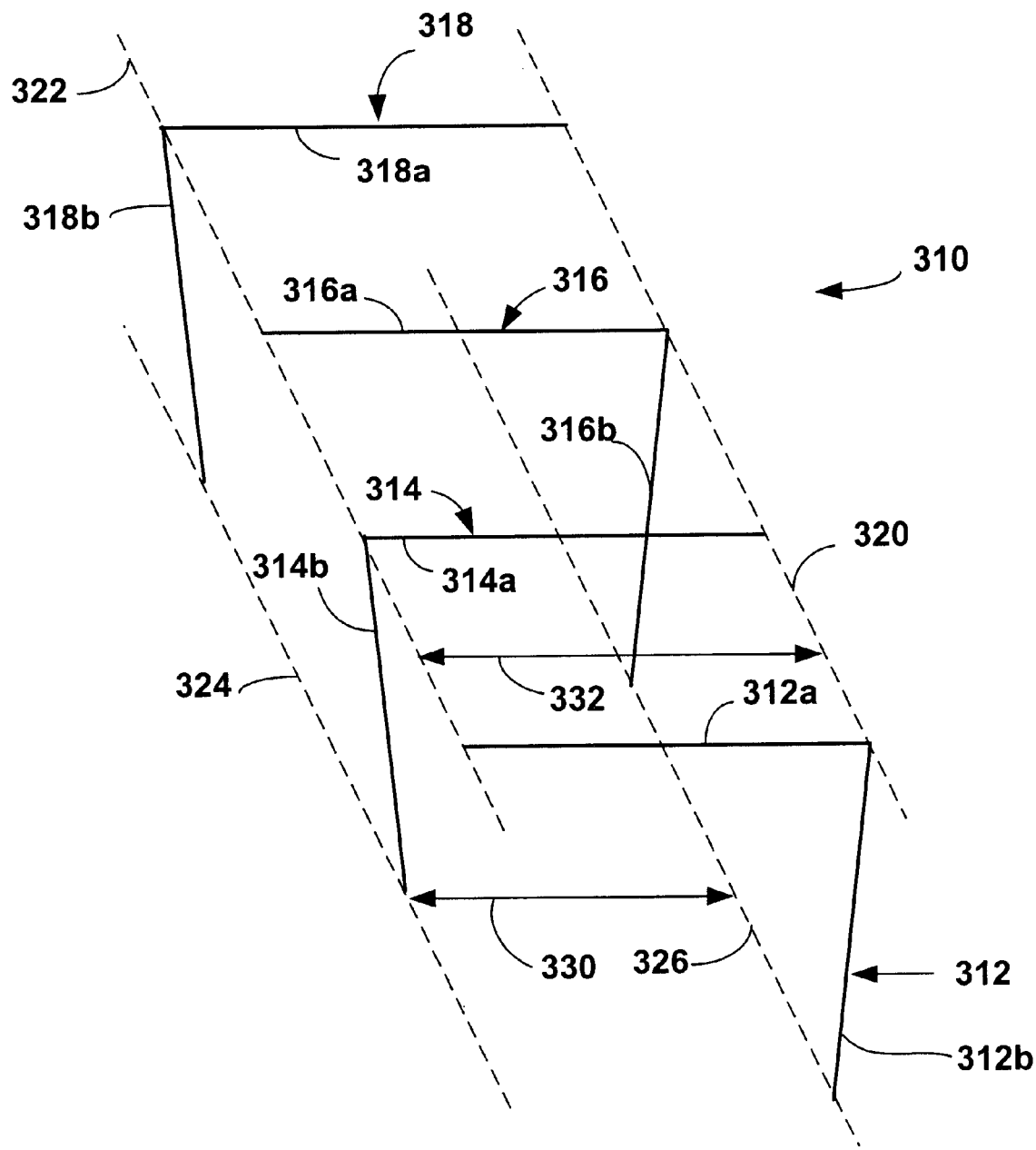
FIG. 3g is a graphical representation of a feature profile formed by aggregating data acquired from a plurality of feature scans in accordance with the present invention.

FIG. 3g illustrates an alternative methodology which may be employed to determine critical dimensions of a feature having a re-entrant profile. In this example, a representation 310 of a feature profile is constructed by aggregating reconstructed portions 312, 314, 316, and 318 of the feature corresponding to measurement data obtained during different measurement intervals. For example, the reconstructed portions 312 and 316 correspond to critical dimension data obtained during scanning intervals in which the beam lines (e.g., an electron beam from a CD-SEM) are oriented at a selected angle relative to the feature being scanned, such as shown and described with respect to FIG. 3c. Similarly, the other reconstructed portions 314 and 318 correspond to measurement data of a feature obtained during scanning intervals in which beam lines are oriented at different angles relative to the feature, such as shown in FIG. 3a. The relative scanning angles that provide reconstructed portions 312 and 316, for example, are substantially opposite the scanning angles that produce reconstructed portions 314 and 318 relative to the feature and substrate.

Each respective reconstructed feature portion 312, 314, 316, 318 has a respective top portion (indicated at 312a, 314a, 316a, 318a) and a side portion (312b, 314b, 316b, 318b) which are proportional to corresponding actual feature dimensions. The other parts of each feature portion are removed (or ignored) as not providing sufficiently reliable indications of the feature dimensions. As mentioned above, this is a result of the scanning angles employed for each respective measurement interval.

The ends and vertex between the top and side portions of each respective reconstructed feature portion 312, 314, 316, 318 define feature boundaries that may be employed to facilitate construction of the representation 310, in accordance with an aspect of the present invention. Specifically, corresponding feature boundaries may be connected by virtual connecting lines 320, 322, 324, and 326 drawn through the respective boundaries of each feature portion. While, for purposes of simplicity of illustration, the virtual connecting lines 320, 322, 324, and 326 are shown to be linear, it is to be appreciated that other line shapes may be employed commensurate with the actual shape of the feature profile. It is also to be appreciated that the longitudinal spacing between adjacent portions 312, 314, 316, 318 is shown for purposes of simplicity of illustration and that the distance between adjacent scan lines may be determined based on the resolution of the scanning tool.

Critical dimensions of the feature may, in turn, be extrapolated from virtual connecting lines 320–326 at any point along the feature representation 310. By way of example, a critical dimension measurement at the juncture of the feature relative to the substrate may be obtained based on the distance of between virtual connecting lines 324 and 326. In particular, a line 330 is drawn to connect the virtual lines 324 and 326 (corresponding to lower feature boundaries). The line 330 extends a distance that is proportional to a critical dimension of a lower portion of the feature, particularly at the juncture where the feature sidewalls meet the substrate.

In order to determine a critical dimension of an upper portion of the feature, another line 332 may be drawn to connect virtual lines 320 and 322. The line corresponds to a cross-sectional feature dimension for an upper feature portion intermediate the scanning intervals where the feature was scanned to obtain portions 321 and 314. In particular, the line 332 extends a distance that is proportional to a critical dimension of the upper feature portion.

Referring to FIG. 4, a CD-SEM system 400 is shown for measuring and/or imaging feature profiles in accordance with the present invention. The system includes a chamber 410 for housing a wafer 420. An electron beam 430 is directed from an electromagnetic lens 440 toward the wafer 420. The electron beam 430 is created from high voltage supplied by a power supply 450 associated with a beam generating system 460 which includes an emission element 470. The power supply 450 provides operating power to the CD-SEM system 400 along with providing a high voltage to the beam generating system 460. Any suitable power supply (e.g., linear, switching) may be employed to carry out the present invention.

The electromagnetic lens 440 includes a field generating device for applying an appropriate electromagnetic field to direct the electron beam at a selected angle relative to the wafer 420. Accordingly, the electron beam 430 may be directed onto the wafer at different angles relative to the wafer during different scanning intervals, such as described in greater detail above (see, e.g., FIGS. 2a, 2b, 3a, and 3c). Various focusing, and scanning elements (not shown) in the beam generating system 460 further guide the electron beam 430 from the emission element 470 to the electromagnetic lens 440. The electron beam particles may be accelerated to energies ranging, for example, from about 500 eV to 40 Kev.

When the electron beam 430 strikes the surface of the wafer 420, electrons and X-rays are emitted which are detected by a detector 480 and are provided to a detection system 490. The detection system 490 provides digitized detector signals to a processing system 500 for performing conventional critical dimension measurements and signal analysis in accordance with the present invention. Electrons which are emitted from the surface of the wafer 420, which are most useful for critical dimension imaging, are known as secondary electrons and provide a substantial amount of the signal current received by the detector 480. A critical dimension measurement and/or image may also be directed to an associated display 510 by the processing system 500. In addition to analyzing data received by the detection system 490, the processing system 500 synchronizes the scanning of the display 510 with electron beam 430 scanning of the wafer 420 to provide the image. A contrast of the displayed image is related to variations in the flux of electrons arriving at the detector 480, which varies based on the yield of emitted electrons from the surface of the wafer 420 relative to the incident electrons from the electron beam 430.

The detection system 490 receives the signals indicative of electron emissions from the wafer surface via the detector 480 and digitizes the information for the processing system 500. In addition, the detection system 490 may also provide filtering or other signal processing of the received signal, as described in more detail below. The processing system 500 provides critical dimension information to the display 510 and/or stores information in a memory 570. The processing system 500 includes a processor (not shown) for controlling the beam generating system 460, providing critical dimension measurements, and for performing signal analysis in accordance with the present invention. It is to be appreciated that a plurality of processors and/or processing systems may be included as part of and/or external to the CD-SEM system 400 for performing signal analysis in accordance with the present invention.

The processor in the processing system 500 also is programmed to control and operate the various components within the CD-SEM system 400 in order to carry out the various functions described herein. The processor may be any of a plurality of processors, such as the AMD Athlon™, K6™, or other type architecture processors. The manner in which the processor may be programmed to carry out the functions relating to the present invention will be readily apparent to those having ordinary skill in the art based on the description provided herein and are omitted herein for the sake of brevity.

The memory 570 is operatively coupled to the processing system 500 and serves to store program code executed by the processor for carrying out operating functions of the system 400 as described herein. The memory 570 also serves as a storage medium for temporarily storing information, such as curve fitting data, critical dimension data, statistical data, and other data which may be employed in carrying out the present invention. The system 400 also may include additional memory.(e.g., non-volatile memory) for storing measurement data and/or images for a wafer under test.

The signals received from scanning the wafer 420 surface are digitized and analyzed as a data set. Analysis of the data, such as, for example, by employing regression mathematics to the data set, produces a shape for the data set corresponding to the feature profile. In particular, each scanning interval produces an feature data set corresponding to part of the feature profile, from which unreliable regions of the feature data (e.g., the side edges of the feature) may be rejected or ignored based on predetermined criteria for the shape of the data set.

FIG. 4 schematically illustrates a cross-sectional area of the wafer 420 corresponding to an etched portion of the wafer that includes two lines 550 and 560. Each of the lines 550, 560 has a re-entrant profile, as described herein. In a conventional system, an accurate profile may not be resolved as the electron beam typically is provided at a single angle that is substantially perpendicular to the wafer surface. In accordance with the present invention, the electron beam is directed at different angles during different scanning intervals, such as according to control signals from the processing system 500. As a result, critical dimensions of the sidewall portion of each line 550, 560 are measured. In particular, the emitted electron beam is provided at appropriate angles during associated scanning intervals so as to strike and interact with the sidewall portions of each line 550, 560. Reflected electrons and X-rays are detected by the detector to provide a signal indicative of each feature of the wafer 420.

As described above, the present invention may be implemented as a software system operating in conjunction with the CD algorithm of the SEM system 400. It is to be appreciated however, that the present invention may be implemented as part of a separate processing system. For example, the critical dimension signal data may be passed to a post or concurrent processing system to determine the critical dimensions for a particular wafer region being measured. It is further to be appreciated that the present invention may be directed to other systems which provide signals based on surface geometry and/or topographical measurements.

A curve fitting analysis is applied to the received data to determine the signal shape (e.g., flat shape, parabolic shape) in the measured region. Many techniques are available for fitting particular data to a linear region or to a curve such as, for example, a linear and/or polynomial regression algorithm to determine the amount of flatness or curvature in the feature region. It is to be appreciated, however, that many other well known methods for curve fitting and/or regression may be applied to determine the shape of the received data and each such method is contemplated as falling within the scope of the present invention.

Figure 5:
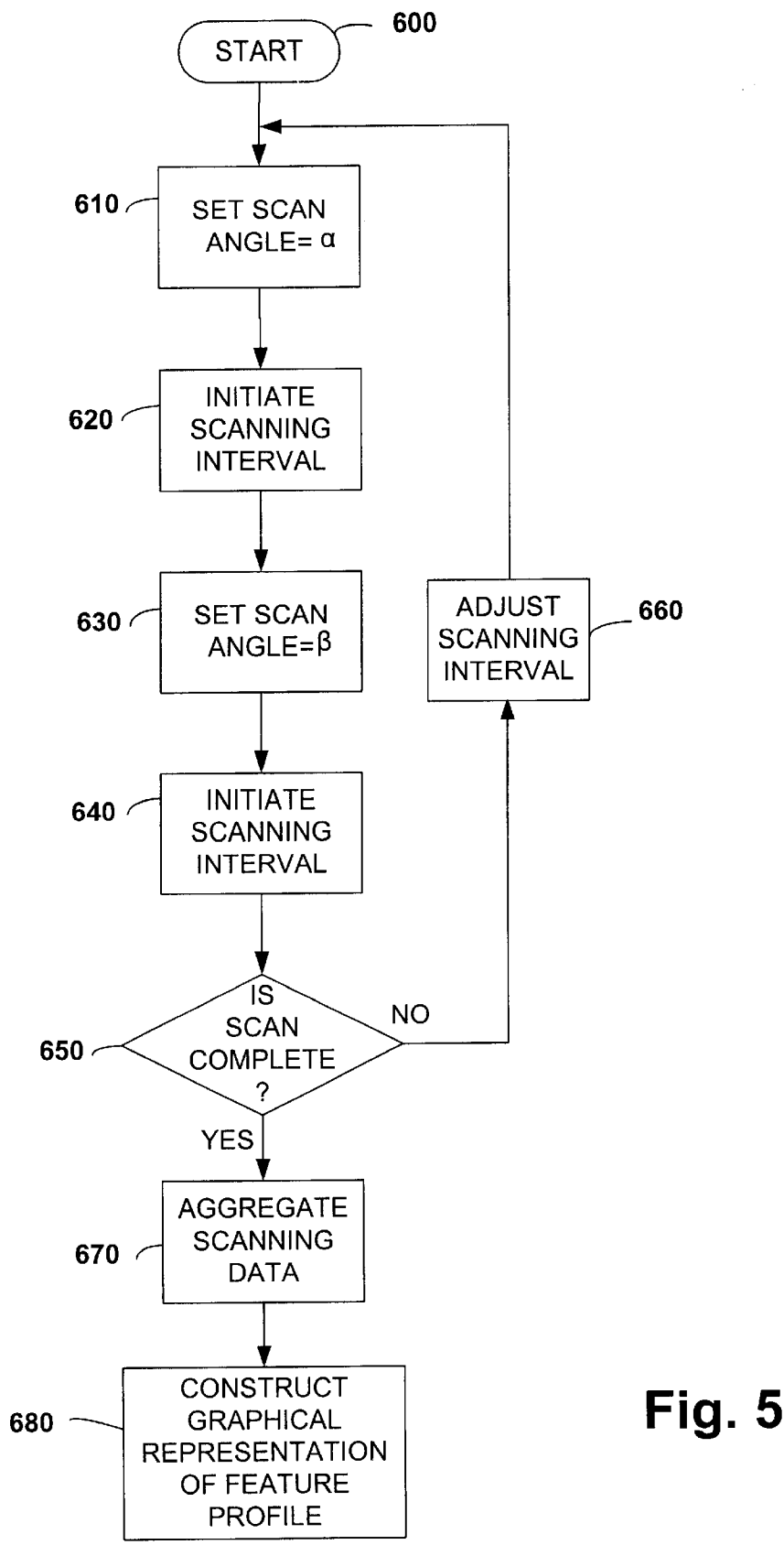
FIG. 5 is a flow chart diagram illustrating a methodology in accordance with the present invention.

In view of the exemplary operating environments and scanning implementations shown and described above, a methodology, which may be implemented in accordance with the present invention, will be better appreciated with reference to the flow diagram of FIG. 5. While, for purposes of simplicity of explanation, the methodology of FIG. 5 is shown and described as a series of steps, it is to be understood and appreciated that the present invention is not limited by the order of steps, as some steps may, in accordance with the present invention, occur in different orders and/or concurrently with other steps from that shown and described herein. Moreover, not all illustrated steps may be required to implement a methodology in accordance with the present invention.

Referring to FIG. 5, the process begins at step 600 in which a substrate, such as a wafer, is positioned in a CD-SEM system for performing measurements thereof in accordance with the present invention. In addition, parameters are initialized and flag conditions are set to their starting values. The process then proceeds to step 610.

At step 610, a scan angle for the electron beam from the SEM is set to a predetermined angle (e.g., scan angle=$\alpha$). The scan angle determines the relative angle at which the electron beam is directed onto the substrate. In accordance with an aspect of the present invention, the angle $\alpha$ is selected so that the electron beam is able to strike and interact with at least one sidewall portion of a feature having a re-entrant profile. Next, the process proceeds to step 620 in which a scanning interval is initiated. The scanning interval may include scanning across a single feature, a region, or across the entire wafer surface. After the scanning interval is completed, the process proceeds to step 630.

At step 630, the scan angle is set to another value $\beta$ which is different from the previous scan angle $\alpha$ ($\beta \neq \alpha$). In accordance with one aspect of the present invention, the scan angle $\beta$ is set to be substantially opposite the angle $\alpha$ relative to a line drawn perpendicular to the substrate (e.g., $\beta = -\alpha$). The angle $\beta$ enables the electron beam to strike the other sidewall portion of the feature having the re-entrant profile. The process proceeds to step 640 in which a next scanning interval is initiated. As mentioned above, the scanning interval may be along the same cross-sectional area of the substrate that the previous scanning interval (step 620) measured or, alternatively, the scanning interval of step 640 may be displaced therefrom by a selected amount. After the scanning interval of step 640, the process then proceeds to step 650.

At step 650, a determination is made as to whether the scanning process is complete. The extent of the scanning process may be selectable by the user. By way of example, the system may be programmed and/or configured to scan one or more selected features of the substrate or to scan the entire surface topography of the substrate. Accordingly, the determination (step 650) may vary according to the selected scanning profile. If the determination is negative, thereby indicating that additional surface topography is to be scanned, the process proceeds to step 660.

At step 660, the scanning interval (e.g., the region over which the electron beam is directed) may be adjusted so as to scan an adjacent (or different) topographical region. The process then returns to step 610 to implement an additional scan. According to an aspect of the present invention, a scan comprises two scanning intervals, with the scan angle being set to different values during each scanning interval.

If the determination at step 650 is positive, thereby indicating that the scan is complete (e.g., based on the selected scanning region), the process proceeds to step 670. At step 670, the measurement data is processed and aggregated to construct an image corresponding to the scanning region. Because during each scanning interval the electron beam is directed at a particular angle relative to the substrate, the measurement data for a given scanning interval may be more accurate for portions of each feature that is scanned. In particular, when the angled electron beam strikes and interacts with a corresponding sidewall portion, it produces an accurate representation for feature characteristics based on such interactions (e.g., feature portions that are visible according to the angled beam). In contrast, if the electron beam is unable to strike a particular part of a feature, the measurement data may be unreliable. As a result, at step 670, the measurement data is aggregated so that the reliable and accurate part of measurement data are stored and data determined too unreliable or inaccurate may be rejected or ignored. The remaining portions of the aggregated measurement data are stored in memory for constructing an image of the feature at step 680. Aggregated data also may be utilized to obtain quantitative measurements of the features, including critical dimensions, profile information, etc. The resulting reconstruction has dimensions that are proportional to the feature being scanned so as to provide accurate cross-sectional feature characteristics. In particular, the reconstruction accurately reflects a lower portion of the feature profile, including at the juncture between the feature and the substrate.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method for measuring a cross-sectional characteristic of a feature associated with a substrate, the method comprising the steps of:

performing first and second scans of the feature at different angles relative to the substrate to provide respective first and second feature data sets, wherein the different angles are opposite to each other relative to an imaginary line drawn perpendicular to the substrate; and aggregating the first and second feature data sets to provide an indication of the feature characteristic.

2. A method for measuring a cross-sectional characteristic of a feature associated with a substrate, the method comprising the steps of:

performing first and second scans of the feature at different angles relative to the substrate to provide respective first and second feature data sets, wherein the first scan is at about one to about five degrees relative to a plane extending perpendicularly through the substrate and the second scan is provided at an angle ranging from about minus one to about minus five degrees relative to the perpendicular plane; and aggregating the first and second feature data sets to provide an indication of the feature characteristic.

3. A method for measuring a cross-sectional characteristic of a feature associated with a substrate, the method comprising the steps of:

performing first and second scans of the feature at different angles relative to the substrate to provide respective first and second feature data sets, wherein the feature extends a length along the substrate, and a plurality of the first and second scans are performed at spaced apart intervals along the feature length; and aggregating the first and second feature data sets to provide an indication of the feature characteristic.

4. The method of claim 1, further comprising constructing a graphical representation of the feature from the first and second feature data sets.

5. A method for measuring a cross-sectional characteristic of a feature associated with a substrate, the method comprising the steps of:

performing first and second scans of the feature at different angles relative to the substrate to provide respective first and second feature data sets;

aggregating the first and second feature data sets to provide an indication of the feature characteristic; and overlaying the first and second feature data sets to determine a cross-sectional dimension of the feature.

6. The method of claim 5, wherein the cross-sectional dimension is at a juncture of the feature and the substrate.

7. The method of claim 1, wherein the feature is a line formed on the substrate.

8. The method of claim 1, wherein a scanning electron microscope is employed to scan the feature at the first and second angles.

9. A method for measuring a feature located on a substrate, the method comprising the steps of:

scanning the feature at a first angle relative to the substrate to provide a first image;

scanning the feature at a second angle relative to the substrate to provide a second image, the second angle being opposite the first angle; and aggregating the first and second images to determine a profile of the feature.

10. A method for measuring a feature having a re-entrant profile located on a substrate, the method comprising the steps of:

scanning along a first path across part of the feature at a first angle relative to the substrate to provide a first image based on the scanning along the first path;

scanning along a second path across part of the feature at a second angle relative to the substrate to provide a second image based on the scanning along the second path, the second path being spaced from the first path, the second angle being different from the first angle; and aggregating the first and second images to determine a cross-sectional characteristic of the feature.

11. The method of claim 10, wherein the feature is elongated and the method further includes the steps of repeating each of the scanning steps for a plurality of different spaced apart paths along the length of the feature.

12. The method of claim 10, further including the step of constructing a representation of the feature from the first and second images.

13. The method of claim 12, further including the step of visually displaying the graphical representation of the feature.

14. The method of claim 10, wherein the cross-sectional characteristic corresponds to a feature dimension at a bottom part of the feature located near the substrate.

15. The method of claim 14, wherein the step of aggregating further includes overlaying the first and second images to provide a cross-sectional dimension of the feature at a juncture of the feature and the substrate.

16. The method of claim 10, further including using a scanning electron microscope to perform the scanning steps.

17. The method of claim 10, wherein the first and second angles are substantially opposite to each other relative to an imaginary line drawn perpendicular to the substrate.

18. A system for measuring a critical dimension of a feature of a substrate, comprising:

a measurement system configured for emitting scanning signals at different, opposite angles relative to the substrate;

wherein the measurement system is configured to determine a first feature data set of the feature based on scanning signals directed at a first part of the feature at a first angle relative to the feature and to determine a second feature data set of a second part of the feature based on scanning signals directed at the second part of the feature at a second angle relative to the feature, the second angle being different from the first angle, an aggregate of the first and second feature data sets determining a profile for the feature, wherein the first and second parts are spaced apart paths that extend across different parts of the feature or include substantially the same path that extends across the feature.

19. The system of claim 18, wherein the measurement system is scanning electron microscope.

20. A system for determining a cross-sectional profile of a feature in a substrate, comprising:

an emitter for directing a beam onto the substrate at a first angle during a first measurement interval and at a second angle, which is different from the first angle, during a second measurement interval, wherein the emitter directs the beam onto the feature along spaced apart paths extending across the feature during the respective measurement intervals;

a detector for detecting interactions between the beam and the substrate and providing a detector signal indicative thereof; and a controller for determining a first feature data set based on the detector signal associated with the first measurement interval and a second feature data set based on the detector signal associated with the beam during the second measurement interval, the controller determining a characteristic of the feature of the wafer based on the first and second feature data sets.

21. A CD-SEM system for measuring a cross-sectional dimension of a feature having a re-entrant profile relative to a substrate, comprising:
 a lens for directing electrons to the surface of the substrate at a first angle during a first scanning interval and at a second angle during a second scanning interval, the second angle being opposite the first angle relative to the substrate;
 a detector for providing a signal based upon electrons received from the surface of the wafer; and
 a processing system for determining a first feature data set based on detected electrons associated with the first scanning interval and a second feature data set based on detected electrons associated with the second scanning interval, the processing system determining a cross-sectional characteristic of the feature based on an aggregation of the first and second feature data sets.

22. A system for measuring a profile of a feature of a wafer, comprising:
 means for directing a plurality of first and second signals onto to the surface of the wafer at opposite first and second angles;
 means for determining a first feature data set based on the plurality of first signals;
 means for determining a second feature data set based on the plurality of second signals; and
 means for determining a cross-sectional characteristic of the feature based on the first and second feature data sets.

* * * * *